United States Patent
Yagi et al.

(10) Patent No.: US 6,635,620 B1
(45) Date of Patent: Oct. 21, 2003

(54) HYDROXYPROLINE DERIVATIVES

(75) Inventors: Akira Yagi, Fukuoka (JP); Takao Shida, Tokyo (JP); Kokushin Ryu, Tokyo (JP); Taiichi Kaku, Tokyo (JP)

(73) Assignee: Japan Bioproducts Ind. Co., Ltd., Tokyo (JP)

( * ) Notice: Subject to any disclaimer, the term of this patent is extended or adjusted under 35 U.S.C. 154(b) by 0 days.

(21) Appl. No.: 09/646,297

(22) PCT Filed: Sep. 4, 1998

(86) PCT No.: PCT/JP98/03993

§ 371 (c)(1),
(2), (4) Date: Dec. 26, 2000

(87) PCT Pub. No.: WO99/47546

PCT Pub. Date: Sep. 23, 1999

(30) Foreign Application Priority Data

Mar. 16, 1998 (JP) .......................... 10-087960

(51) Int. Cl.[7] ...................... A61K 31/495; A61K 38/05; C07D 487/04; C07K 5/062
(52) U.S. Cl. .......................... 514/19; 514/249; 544/349
(58) Field of Search ................... 424/439, 442, 424/584; 426/656, 657; 435/1.1, 1.2, 1.3, 68.1; 514/19, 20, 249; 530/343; 544/349; 548/533, 538

(56) References Cited

U.S. PATENT DOCUMENTS 3,832,465 A * 8/1974 Ghadimi .................. 514/19
6,017,884 A * 1/2000 Ichida et al. .............. 514/12

FOREIGN PATENT DOCUMENTS

| JP | A2186994 | 7/1990 |
| JP | A532533 | 2/1993 |
| JP | A543408 | 2/1993 |

| WO | 97/17991 | * 5/1997 |

OTHER PUBLICATIONS

Rosen et al., Int. J. Peptide Protein Res., vol. 35, No. 6, pp. 545–549 (1990).
Jandke et al., J. Chromatogr., vol. 382, pp. 39–45 (1986).
Kodama et al., Anal. Chim. Acta, vol. 352 Nos. 1–3, pp. 141–153 (1997).
Charpentier et al., Clin, Chim. Acta, vol. 138, No. 3, pp. 299–308 (1984).

(List continued on next page.)

*Primary Examiner*—Jeffrey E. Russel
(74) *Attorney, Agent, or Firm*—Birch, Stewart, Kolasch & Birch, LLP

(57) ABSTRACT

The present invention relates to hydroxyproline derivatives represented by the following general formulas and the therapeutic agent containing the same for the impaired organs and tissues.

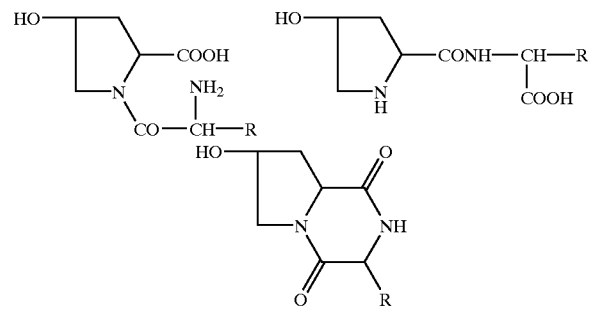

(wherein R is hydrogen or optionally substituted alkyl)

The hydroxyproline derivatives of the present invention possess cell-proliferative and cell-protective activities, and are effectively applied for the restoration and regeneration of impaired organs and tissues.

3 Claims, 11 Drawing Sheets

OTHER PUBLICATIONS

Alexandrou et al., Biochem. Int., vol. 21, No. 2, pp. 271–278 (1990).

Zanaboni et al., J. Chromatogr., vol. 683, No. 1, pp. 97–107 (1996).

Aonuma et al., J. Pharmacobio–Dyn., vol. 5, No. 1, pp. 40–48 (1982).

Chemical Abstract, vol. 51, 1037I (1957).

* cited by examiner

Fig.1
(A) HPLC profile of Laennec
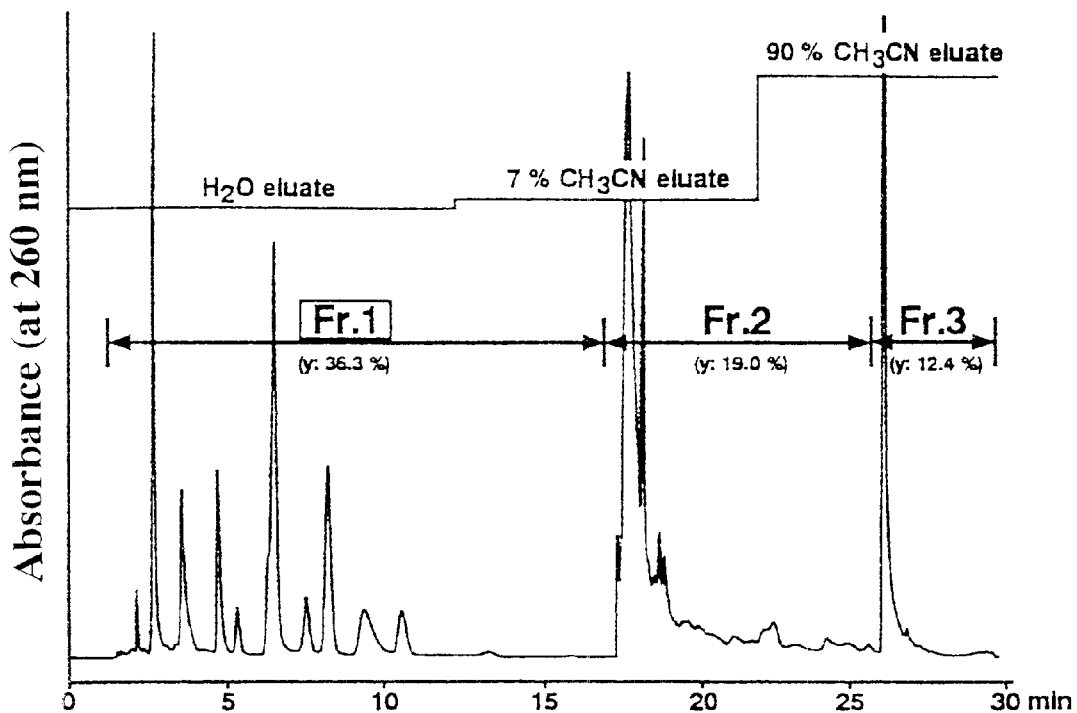
(B) Cell proliferation activity of various fractions of Laennec
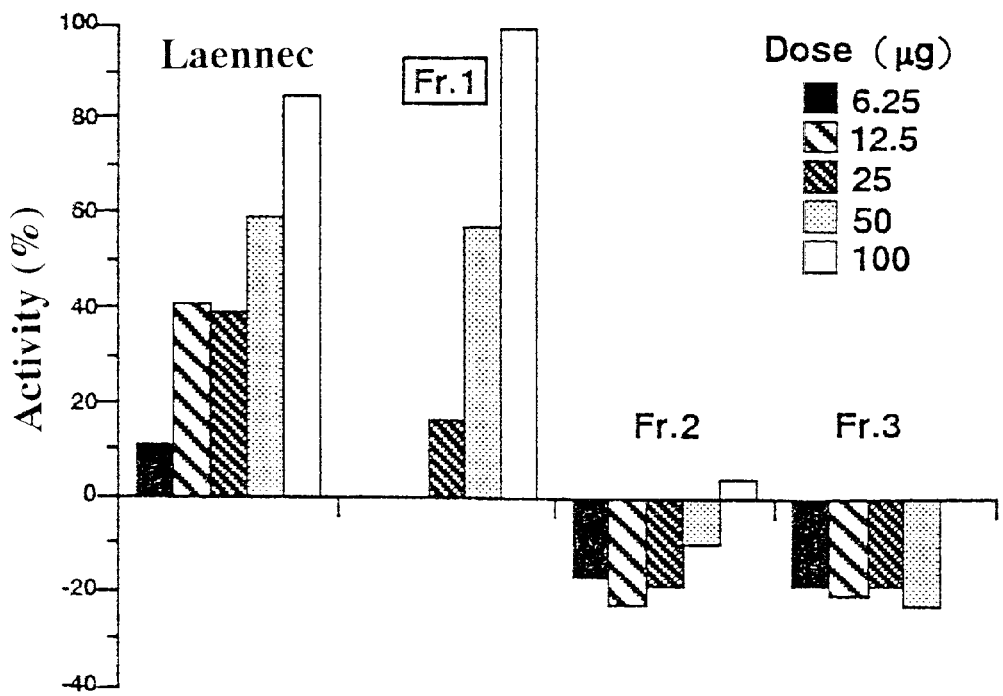

Fig. 2
(A) Profile of Fraction 1 separated by HPLC
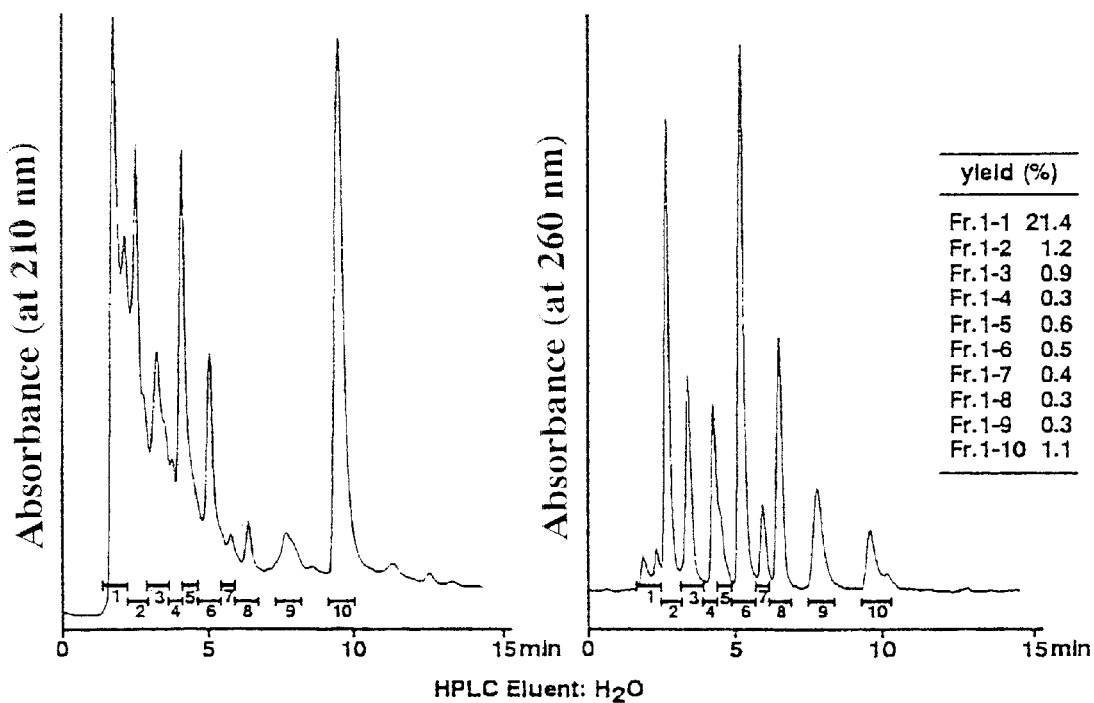
(B) Cell proliferation activity of various fractions of Fraction 1
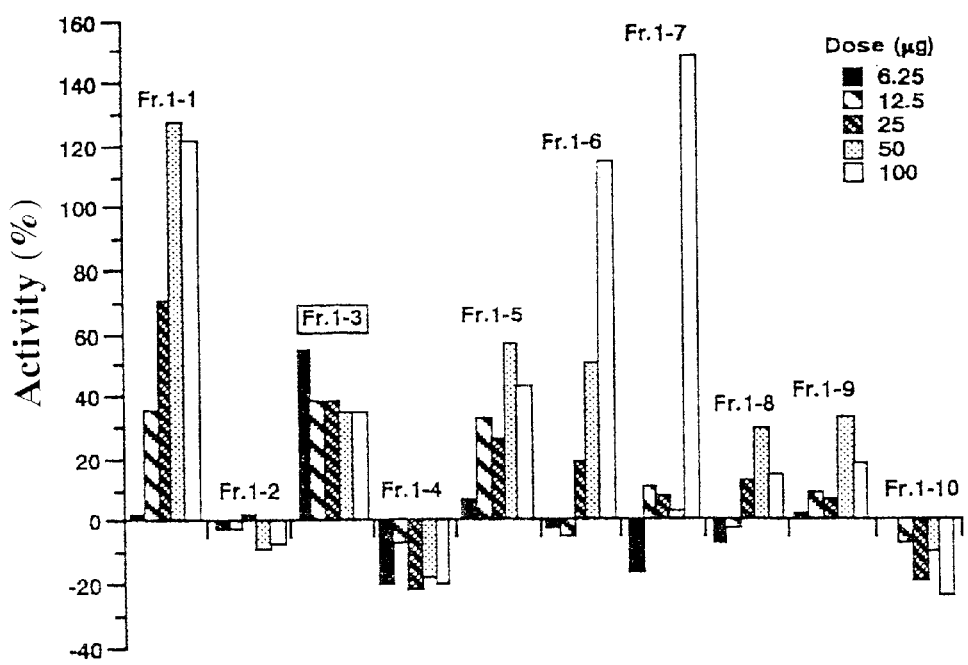

Fig.3
(A) Profile of Fraction 1-3 separated by HPLC
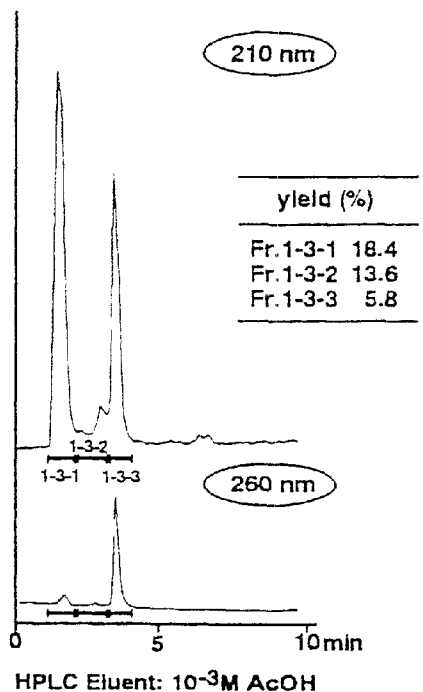
(B) Cell proliferation activity of various fractions of Fraction 1-3
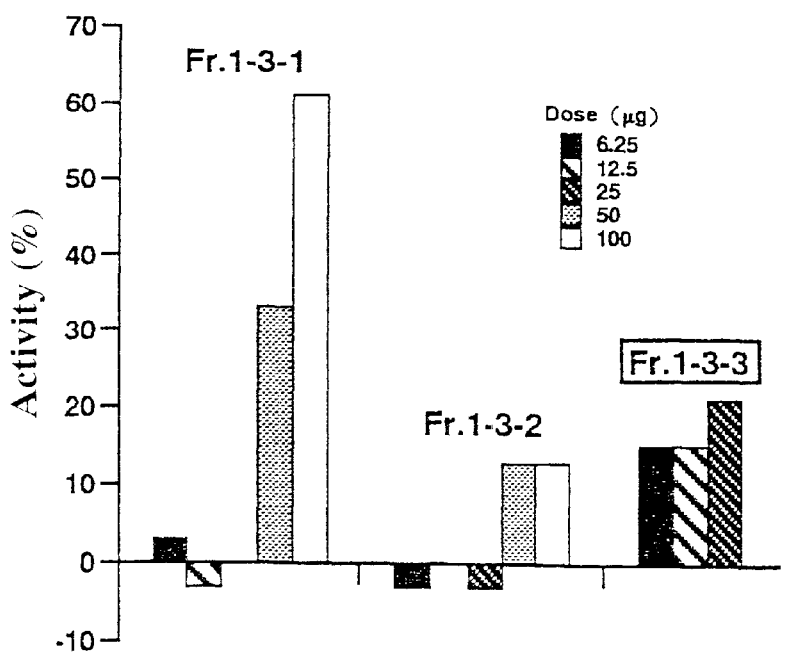

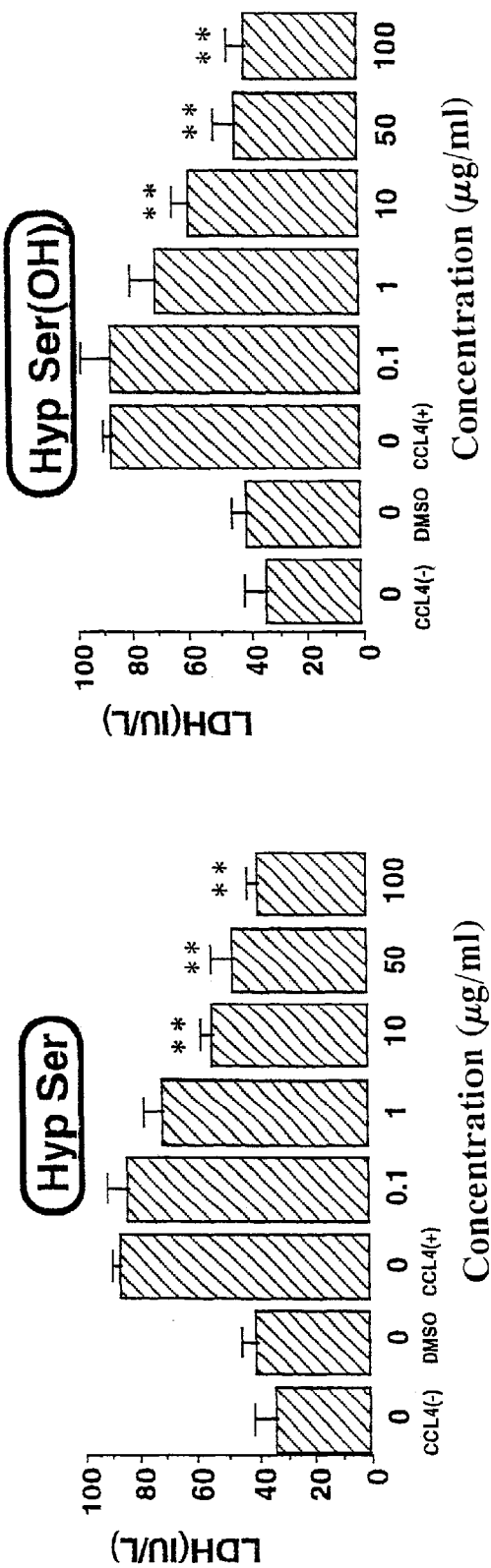
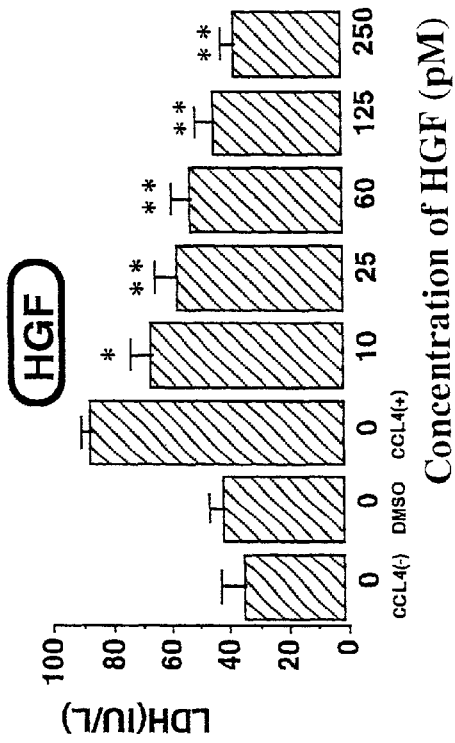
Fig.11

HYDROXYPROLINE DERIVATIVES

TECHNICAL FIELD

This invention relates to hydroxyproline derivatives or their salts, to a therapeutic agent containing hydroxyproline derivatives or their salts for damaged organs and tissues, and to a method of treatment for damaged organs and tissues by administration of hydroxyproline derivatives or their salts.

BACKGROUND ART

It is well known that human placenta and its hydrolysate contain various biologically active substances. For instance, "tissue therapies" with the hydrolysate of human placenta prepared by Filatov's method have been used to treat chronic diseases such as asthma, rheumatism, hepatitis and anti-aging for its proliferative effect on elastic fibroblasts of blood vessels and myofibroblasts.

While human placenta and its hydrolysate are inferred to contain various biologically active substances as mentioned above, their primary effective substances are not yet known. Consequently, in the course of separating, purifying, and identifying the biologically active substances in the hydrolysate of human placenta, the inventors found hydroxyproline derivatives having cell-proliferative and cell-protective activities.

Based on these findings, the purposes of this invention are to provide novel hydroxyproline derivatives which stimulate the proliferation of cells, and to provide a therapeutic agent for damaged organs and tissues, which contain such hydroxyproline derivatives.

DESCRIPTION OF THE INVENTION

The compounds of this invention are hydroxyproline derivatives represented by the following general formulas (1) and (2) or their salts.

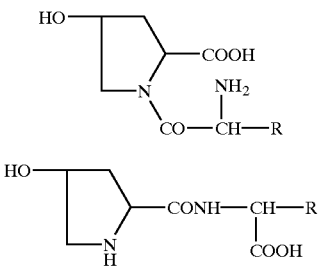

(wherein R is hydrogen or alkyl group which may be substituted with hydroxy group, amino group, carboxy group, aminocarbonyl group, guanidino group, heterocyclic group, mercapto group, alkylthio group or phenyl group optionally substituted with hydroxy group)

In this invention, the therapeutic agent for damaged organs and tissues contains a hydroxyproline derivative represented by the following general formula (1), (2) or (3) or their salts, as an effective ingredient.

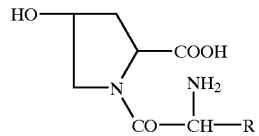

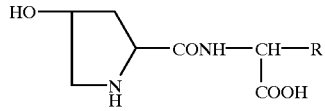

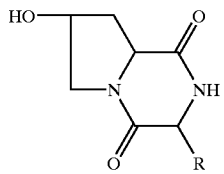

(wherein R is the same as defined above)

The present invention also relates to the method of treatment for damaged organs and tissues comprising administration of an effective amount of hydroxyproline derivative represented by the above-mentioned formula (1), (2) or (3) or their salts, and a use of hydroxyproline derivative represented by the above-mentioned formula (1), (2) or (3) or their salts for manufacturing the therapeutic agent for damaged organs and tissues.

Further, as for the hydroxyproline derivatives represented by the general formulas (1), (2) and (3), the compounds in which R is hydroxymethyl are speculated to be the most useful.

BRIEF DESCRIPTION OF DRAWINGS

FIG. 1 shows the HPLC profile of hydrolysate of human placenta (Laennec, trade name, manufactured by Japan Bioproducts Industry Co., Ltd.) (A), and the cell proliferation activity of its various fractions (B).

FIG. 2 shows the profile of Fraction 1 separated by HPLC (A), and the cell proliferation activity of its various fractions (B).

FIG. 3 shows the profile of Fraction 1–3 separated by HPLC (A), and the cell proliferation activity of its various fractions (B).

FIG. 11 shows the changes in hepatic cytosolic enzyme (LDH) activity in the medium of $CCl_4$-treated primary cultured rat hepatocytes by the compounds of the invention and HGF.

BEST MODE CARRYING OUT THE INVENTION

Figure 4:
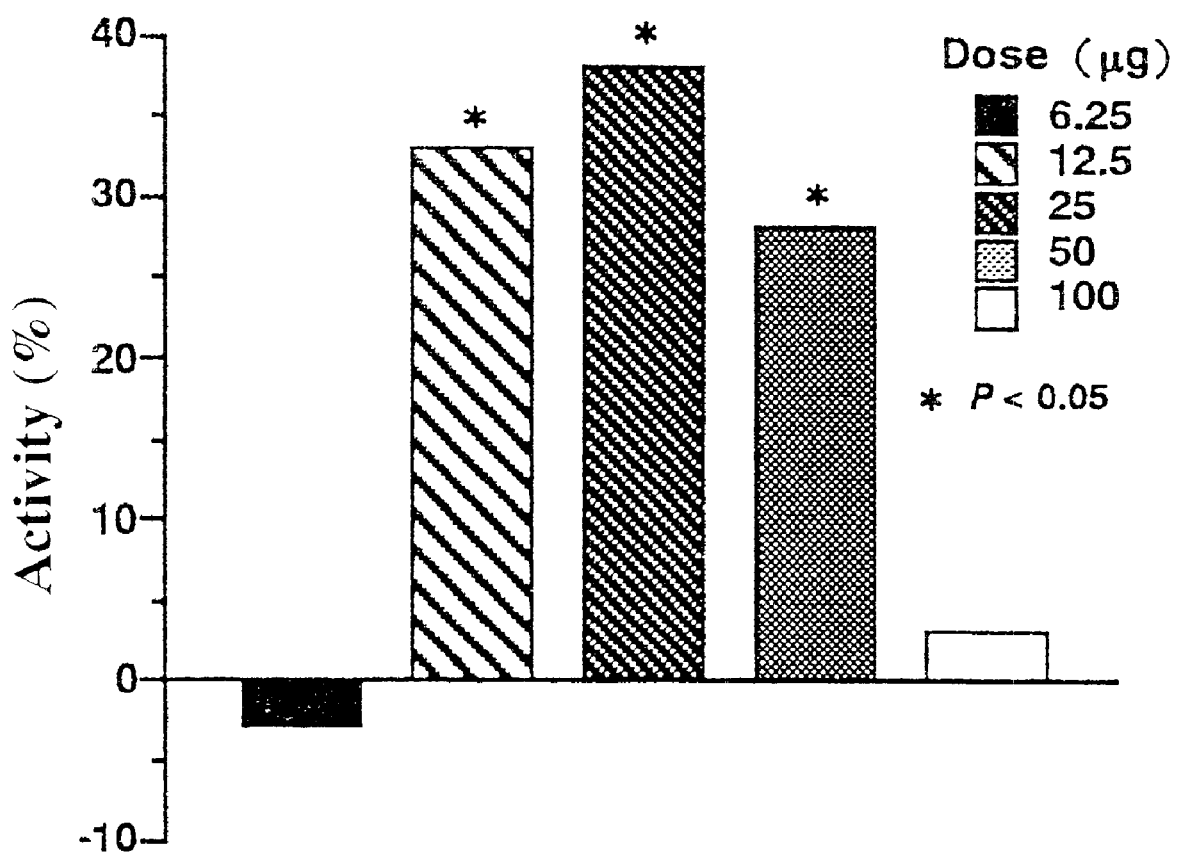
FIG. 4 shows the activity of BHK-21 cell proliferation by the compound of the invention.

In the compounds of the formulas (1), (2) and (3), R is hydrogen or alkyl group. In the alkyl group, those having straight or branched chains with 1–7 carbon atoms are preferable. Suitable examples of the alkyl group may be methyl, ethyl, n-propyl, iso-propyl, n-butyl, iso-butyl, tert-butyl, n-pentyl, n-hexyl, 1,2,2-trimethylpropyl, 2-methylpropyl, 1,1-dimetylpropyl and the like. These alkyl groups also may contain hydroxy group, amino group, carboxyl group, aminocarbonyl group, guanidino group, heterocyclic group, mercapto group, alkylthio group, and phenyl group optionally substituted with hydroxy group, as substituents. Further, among these, imidazolyl and indolyl are exemplified in the heterocyclic group, while methylthio and ethylthio in the alkylthio group, and phenyl and 4-hydroxyphenyl in the phenyl group are the examples in the respective groups.

Salts of the compounds of the formulas (1), (2), and (3) may be any salts as far as pharmacologically non-toxic. These salts may include salts with inorganic acids (e.g. hydrochloric acid, hydrobromic acid, phosphoric acid, sulfuric acid, etc.); salts with organic acids (e.g. acetic acid, succinic acid, maleic acid, fumaric acid, malic acid, and tartaric acid, etc.); salts with inorganic base (e.g. sodium, potassium, calcium, ammonium, etc.); salts with organic base (e.g. triethylamine, arginine, etc.).

The compounds of the formulas (1), (2) and (3) may have asymmetric centers and cyclic rings. The compounds of the invention may include all of the optical and geometrical isomers with asymmetric centers and cyclic rings.

The compounds of the formulas (1), (2) and (3) can be isolated from the hydrolysate of human placenta as mentioned later. However, in general, the compounds of the formulas (1), (2) and (3) are sy,nthesized b)a various chemical methods. For instance, the compounds can be prepared by the following methods.

Reaction process-1

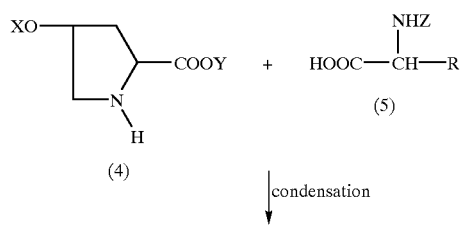

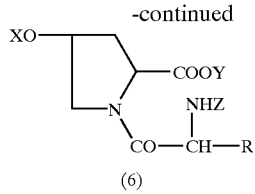

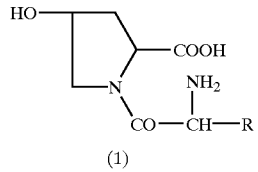

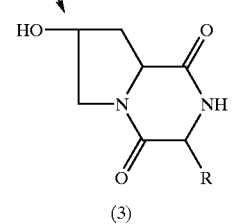

Reaction process-2

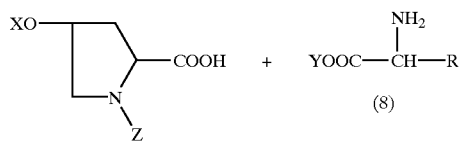

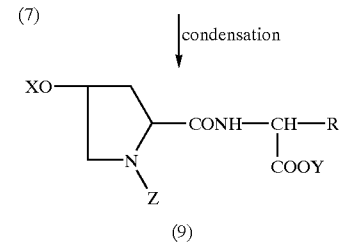

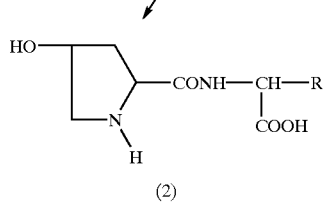

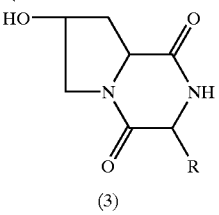

(In Reaction processes-1 and -2, R is the same as defined before, X is a protective group for hydroxy group, Y is a protective group for carboxy group, and Z is a protective group for amino group)

In Reaction process-1, the compound (6) is synthesized through the condensation of hydroxyproline (4), in which the hydroxy and carboxy groups are protected by the ordinary protective groups, and the a-amino acid compound (5), in which the amino group is protected by the ordinary protective group. Such condensation is effectively performed by the conventional amide-reaction such as methods using condensation reagents (e.g. dicyclohexylcabodiimide, etc), methods using activated esters, and the like. And the compounds (4) and (5) having protective groups are also prepared by conventional synthetic methods. The forementioned α-amino acid compound ma)y include serine, alanine, arginine, aspartic acid, asparagine, glutamic acid, glutamine, cysteine, glycine, histidine, leucine, isoleucine, lysine, methionine, valine, ornithine, threonine, phenylalanine, tyrosine, tryptophan and the like.

The compound (6) thus obtained can be converted to the compound (1) of the invention by eliminating the protective groups through known methods.

Further, the compound (6) can be converted to the compound (3) of the invention by a process comprising the steps: eliminating the protective groups for carboxyl and amino of the compound (6), cyclizing through a conventional amide formation method, and then eliminating the protective group for hydroxy.

The compounds (2) and (3) can be obtained by processing the compound (9) with Reaction process-1, wherein the compound (9) is synthesized by Reaction process-2 from the compounds (7) and (8). The amide formation and cyclization in this reaction process are carried out by the same procedures as done in Reaction process-1.

Further, in Reaction processes-1 and -2, the amide formation and the cyclization can be also performed without any protection of hydroxy group.

The compounds (1), (2) and (3) show cell-proliferative and cell-protective activities, and are effective in restoration and proliferation of damaged organs and tissues, especially of a liver (hepatocytes), as shown in Examples mentioned latter. Thus, the compounds of the invention are useful as therapeutic agents-for damaged tissues and organs not only for a human but also for other mammals (for instance, bovines, pigs, horses, sheep, rabbits, monkeys, dogs and cats, etc.).

The efficacy which is expected for the compounds of the invention is illustrated as follows:
(1) Decrease in activities of cytosolic enzymes (GOT, GPT, γ-GTP, ALP, LAP and LDH, etc.) in a damaged liver.
(2) Increase in the hepatic uptake of bilirubin.
(3) Hepatoprotection (prevention. and suppression of degeneration and necrosis of hepatocytes).
(4) Suppression of hepatofibrosis and hyperplasia of hepatic fibrous tissue, and absorption of hyperplastic hepatic fibrous tissue and interstitial connective tissues.
(5) Anti-hepatolipocytosis (decrease in lipid precipitation to a liver and improvement of lipid degeneration in hepatocytes).
(6) Activation of tissue respiration (Activation of succinic acid dehydrogenase and stimulation of tissue respiration in a liver, and activation of metabolism in hepatocytes)
(7) Stabilization of hepatocyte membrane Based upon the above mentioned efficacy and functions, the present therapeutic agent for damaged tissues and organs containing the compound (1), (2) or (3) or their salts as active substances, is utilized as medicines for a human and mammals, especially for their hepatic diseases, for example, preventing the processes from hepatitis to cirrhosis (both A- and B-type cirrhosis), or from cirrhosis to hepatoma, and suppressing the fibrosis and lipocytosis formation in a liver.

The therapeutic agent of the present invention is prepared by mixing the compound (1), (2) or (3) or their salts with pharmacologically appropriate kinds and amounts of additives such as carriers, vehicles and diluents, making them into various forms of drugs such as powders, granules, tablets, capsules, injection and ointments, and being administered orally or non-orally.

The therapeutic agent mentioned above contains a clinically effective amount of the compound (1), (2) or (3), or their salts. The effective doses can be controlled adequately depending upon the administration route, the symptoms, body weight and age of the patient. In general, the agent can be administered once to several times a day at the range of 0.5–100 mg per body weight kg.

INDUSTRIAL APPLICABILITY

The compounds of the present invention possess cell-proliferative and cell-protective activities, and are, therefore, effective in restoration and regeneration of damaged organs and tissues. The therapeutic agent of the present invention contains such compounds as mentioned above, and can be used to treat damaged organs and tissues, especially for the treatment of liver diseases.

EXAMPLES

Examples and Experimental Examples outlined below are solely given for the purpose of illustration and are not to be construed as limitation of the present invention.

The following materials and instruments were used for the present experiments.
(1) Human Placenta Hydrolysate Human placenta hydrolysate, Laennec (trade name, Japan Bioproducts Industry Co., Ltd.) was used. Laennec is prepared from human placenta defatted with acetone, followed by hydrolysis with hydrochloric acid.
(2) High Performance Liquid Chromatography (HPLC) Analysis Conditions The HPLC analysis conditions are as followed:

Column: COSMOSIL $5C_{18}$—AR (4.6 I.D.×150 mm)

Detection: 210, 260 nm

Flow rate: 1.0 ml/min

Temperature: at room temperature (26° C.)

Three-dimensional chromatography:
 Waters 991J Photo-Diode Array Detector
(3) Instruments for Analysis $^1H$ and $^{13}C$ -NMR: JEOL Lambda 500

Optical rotation: JASCO DIP-140

FAB-MS: JEOL HX-110 and Matrix (glycerol)

HR-FAB-MS: JEOL HX-110 and Matrix (triethylene glycol)

Peptide sequencer: Model 470-A (Applied Biosystems)

Amino acid analyzer: Type 835
(4) Measurement of Cell Growth Activity

Cell growth activities of the samples were measured as BHK (baby hamster kidney) −21 cell proliferation activity, following the known method (Planta Med., 62,115–118, 1996, and others). In detail, BHK-21 cells ($1\times10^4$) were cultured in Eagle's minimum essential medium supplemented with 5% fetal bovine serum and 2 mM glutamine, for 3 days at 37° C. with different concentration ($\mu g/ml$) of test samples in 5% $CO_2$/air at pH 7.2. The cells were treated with a mixture of trypsin and 0.02% EDTA solution to detach the cells from each well. The cells were harvested and the numbers of total viable cells were counted. The viability of the cells was determined by the method of dye-exclusion test using 0.4% trypan blue solution. The cell growth activity (%) was determined by comparing with the control cells (medium control).

Example 1
Isolation and Purification of the Compound of the Invention From Human Placenta Hydrolysate Laennec solution was separated into three fractions (Fr.1 to 3) by HPLC. FIG. 1A shows the result of HPLC analysis.

The cell growth activities for BHK-21 cells by Fractions 1 to 3 obtained were measured, and the results were shown in FIG. 1B. As shown in FIG. 1B, Fraction 1 showed the cell growth activity. Fraction 1 showing the cell growth activity was further separated into Fractions 1 to 10 by HPLC. Fractions 1 to 10 were separated according to the elution with water. FIG. 2A shows the results of the HPLC pattern. For Fractions 1 to 10 obtained, the cell growth activities against BHK-21 cells were measured. FIG. 2B shows the results of measurement. Fraction 1–3 showed the cell growth activity at the lower doses of 6.25, 12.5 and 25 μg. Since Fraction 1–3 showed the cell growth activity, this fraction was subjected to HPLC, eluting with $10^{-3}$ M of acetic acid to provide three fractions (Fr. 1-3-1 to Fr. 1-3-3). FIG. 3A shows the results of HPLC pattern. For three fractions obtained, the cell growth activities against BHK 21-cells were measured. As shown in FIG. 3B, Fr. 1-3-3 revealed the cell growth activities at the lower doses of 6.25, 12.5 and 25 μg. Based on the results obtained, preparative HPLC using Cosmosil 75$C_{18}$-PREP (Column: 4.6 I.D.×150 mm, Elution: water) of Laennec (62.7 g of lyophilization) was carried out to provide the cell growth active fractions, in which retention time showed at 3.1 to 3.3 min. by HPLC. The separated fraction (9.4 g) was chromatographed on Sephadex LH-20 (Column: 3 I.D.×85 mm, Elution: water) to provide Compounds 1 (6.2 mg) and 2 (7.6 mg). The cell growth activity of Compound 2 for BHK-21 cells was measured. The results were shown in FIG. 4. As shown in FIG. 4, Compound 2 showed the cell growth activity. While the closer analyses revealed that Compound 1 was uracil, Compound 2 showed the following analytical data.

(1) $[\alpha]_D = -157.9$ degree (C=1.129, water, 25° C.)
(2) Ninhydrin reaction: Positive
(3) Amino acid analysis: a peptide composed of hydroxyproline and Serine at a ratio of 1:1.
(4) Amino acid sequence by amino acid sequencer: N-terminal of the peptide is blocked.
(5) L-Serine and 4-trans-L-Hydroxyproline were identified by Chiral HPLC analysis of the acid hydrolysate.

Based on these analytical data, the structure of Compound 2 was speculated to be 3'-Hydroxymethyl-4-hydroxypyrrolido [1,2-f] 2', 5'-piperazinedione, represented by the formula (3-1);

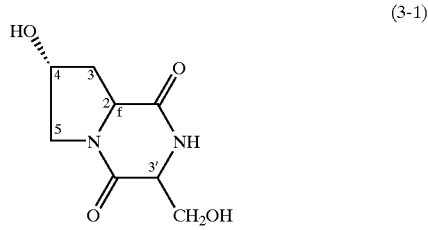

(3-1)

Furthermore, the results obtained by the following instrumental analyses fully supported the above structure.

(6) FAB-MS m/z 201[M+1]$^+$
(7) HT-FAB-MS $C_8H_{12}N_2O_4$
    Found : 201.08730 [M+1]$^+$
    Required: 201.08748
(8) $^1$H NMR (DMSO-$d_6$): δ 1.86 (1H, dd, J=12.5, 6.5), 2.05 (1H, dd, J=12.5, 5.0), 3.20 (1H , dd, J=12.5), 3.56 (1H, dd, J=12.5, 4.0), 3.68 (1H, dd, J=10.0, 5.2), 3.70 (1H, dd, J=10.5, 5.2), 4.07 (1H, t, J=4.0), 4.29 (1H, t, J=5.2), 4.36 (1H, dd, J=5.0, 6.0).
(9) $^{13}$C NMR (DMSO-$d_6$): δ 56.8 (C-2), 37.2 (C-3), 66.7 (C-4), 53.7 (C-5), 56.7 (C-3'), 59.8 (—CH$_2$OH).

As for the compounds represented by the general formulas (1) and (2), the compounds in which R was hydrox) methyl were separately synthesized, and were tested for the cell growth activities against BHK-21 cells. And these newly synthesized compounds were all confirmed to possess such activities.

Experimental Example 1
Effect on Cytosolic Enzyme Activities in Serum of ANIT-treated Rats ANIT (α-naphthylisothiocyanate) dissolved in olive oil was injected intraperitoneally into rats at a dose of 50 mg/kg body wt. For intravenous administration, hydroxyproline derivatives of the invention (1.36 and 6.25 mg/kg in 0.25 ml dissolved in saline) were administered through the penis vein. For oral administration, hydroxyproline derivatives of the invention (6.25 and 25 mg/kg in 2.0 ml dissolved in saline) were administered. The administrations of derivatives were performed at 30 min. before and 8, 24, 36, 46 h after the ANIT treatment. Blood was collected from celiac artery at 47 h after the ANIT treatment. After centrifugation (3500 rpm for 15 min.), the activities of cytosolic enzymes, such as GPT (glutamic-pyruvic transaminase), ALP (alkaline phosphatase), LAP (lactate dehydrogenase) and γ-GTP (γ-glutamyl transferase), and the total bilirubin concentration (BIL) in the serum were measured using the appropriate assay kits (Wako Pure Chemical Industries, JP). As for the hydroxyproline derivatives, the compounds represented by the formulas (3) (wherein R is hydroxymethyl, hereinafter referred to as "Hyp Ser") and (2) (wherein R is hydroxymethyl, hereinafter referred to as "Hyp Ser OH") were used in this experiment.

Figure 5:
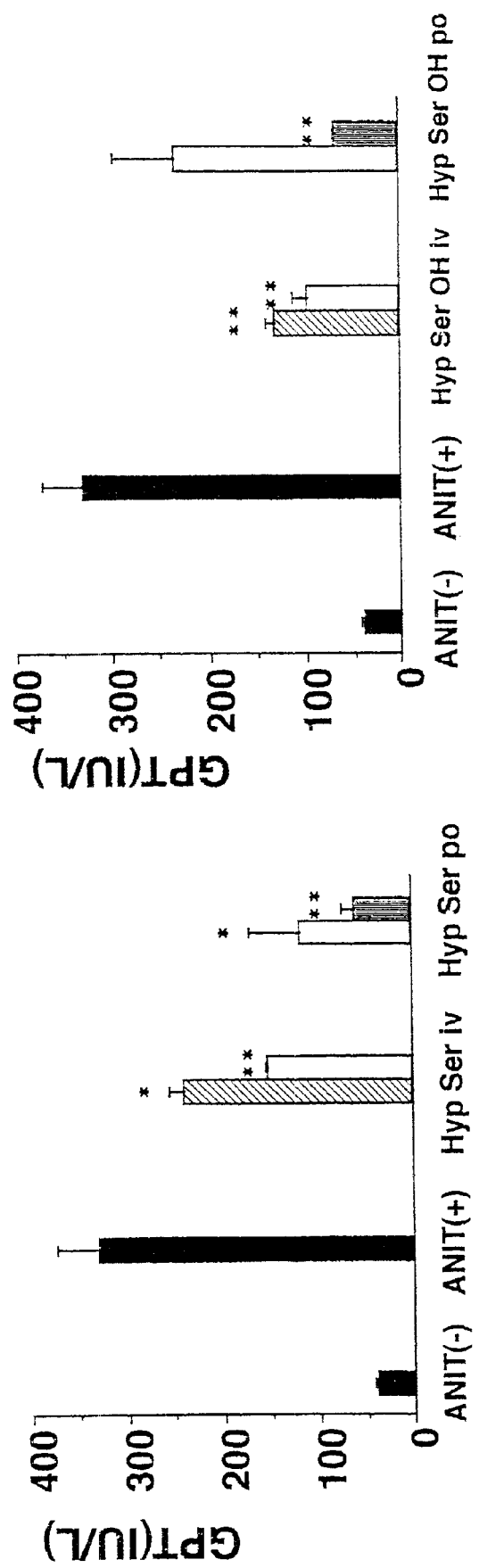
FIG. 5 shows the changes in hepatic cytosolic enzyme (GPT) activity in the serum of ANIT($\alpha$-naphthylisothiocyanate)-treated rats after the administration of the compounds of the invention.
Figure 6:
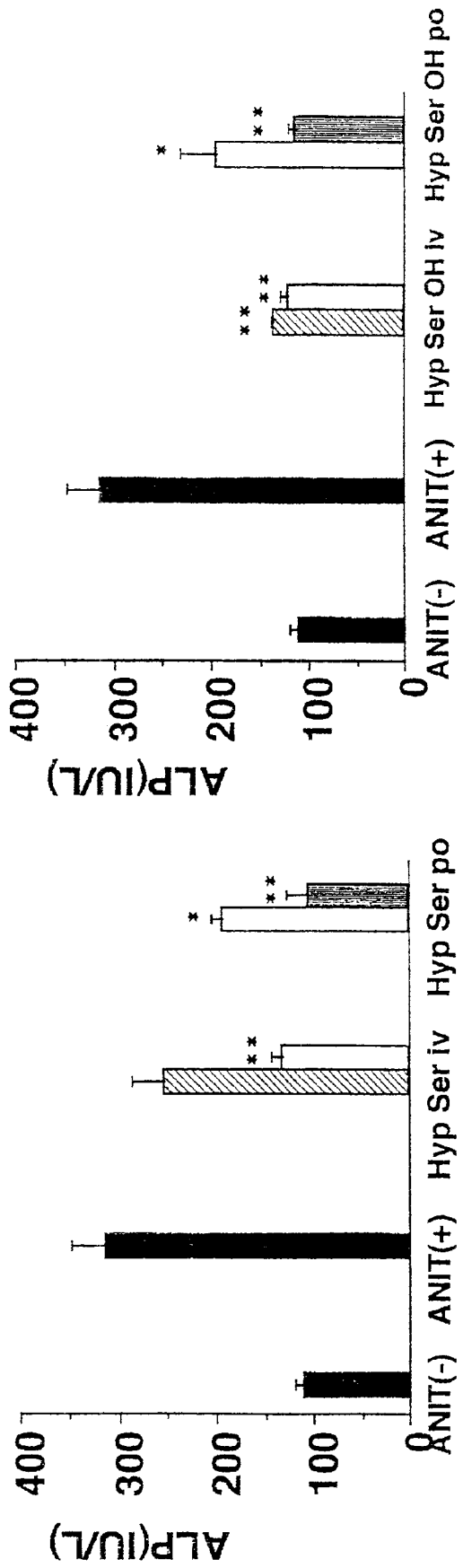
FIG. 6 shows the changes in hepatic cytosolic enzyme (ALP) activity in the serum of ANIT-treated rats after the administration of the compounds of the invention.
Figure 7:
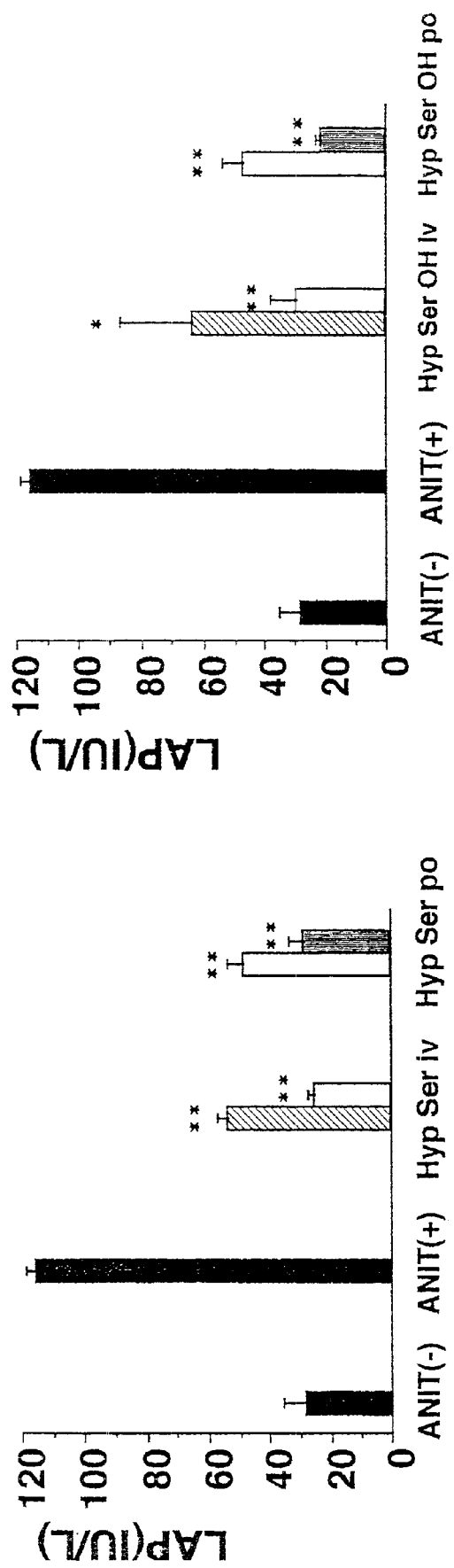
FIG. 7 shows the changes in hepatic cytosolic enzyme (LAP) activity in the serum of ANIT-treated rats after the administration of the compounds of the invention.
Figure 8:
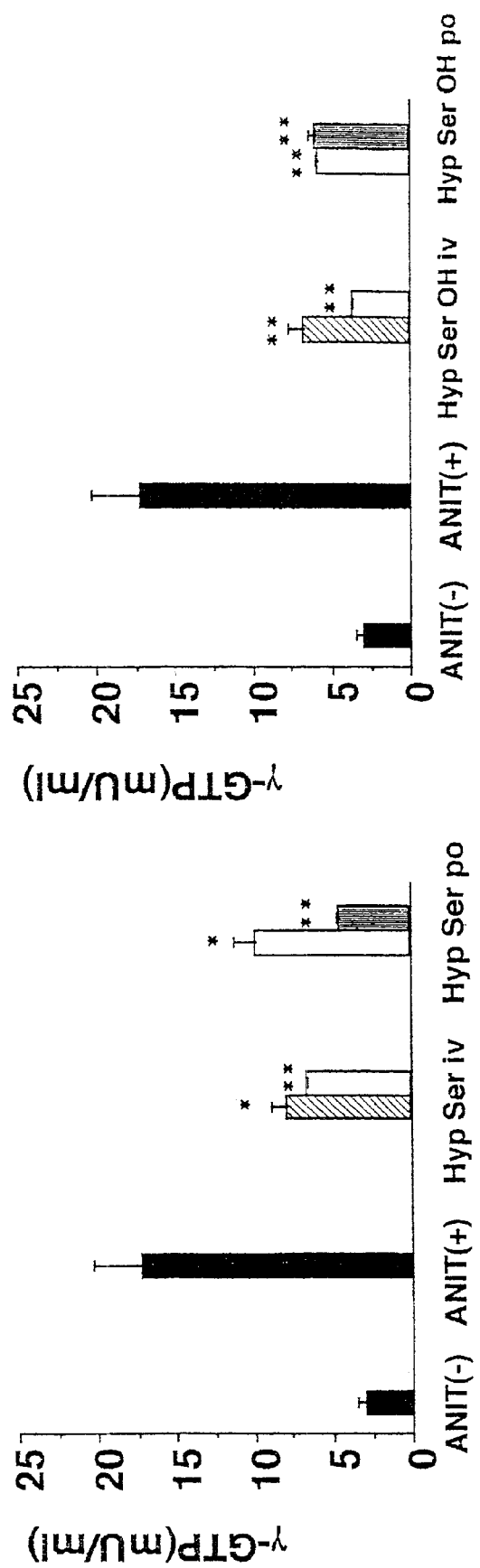
FIG. 8 shows the changes in hepatic cytosolic enzyme ($\gamma$-GTP) activity in the serum of ANIT-treated rats after the administration of the compounds of the invention.
Figure 9:
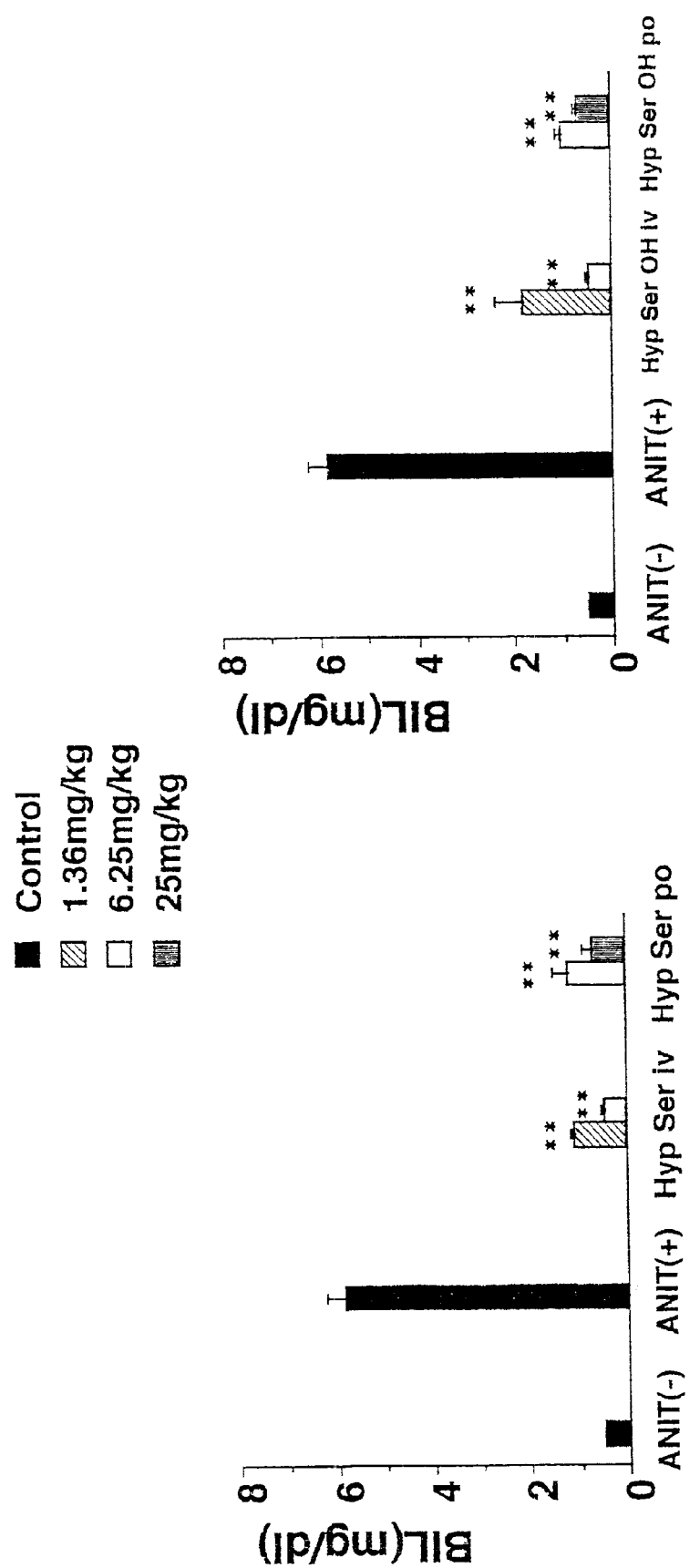
FIG. 9 shows the changes in BIL (bilirubin) concentration in the serum of ANIT-treated rats after the administration of the compounds of the invention.

The results were shown in FIG. 5 (GPT), FIG. 6 (ALP), FIG. 7 (LAP), FIG. 8 (γ-GTP), and FIG. 9 (BIL). The values in these results were expressed as average ± SE of three animals. Statistical analysis was performed by Student's t-test to identify significant differences between various treatment groups. The control was the group with the administration of ANIT alone. * expresses p<0.05, and ** p<0.01.

As shown in the figures, the hydroxyproline derivatives of the invention decreased the abnormal cytosolic enzyme activities in the damaged liver, and thus indicated to improve the liver functions.

Experimental Example 2
Effect on Cytosolic Enzyme Activities in Medium of $CCl_4$-treated Primary Cultured Rat Hepatocytes Hepatocytes were isolated based on the Nakamura's method (The Experimental Methods of Primary Cultured Hepatocytes, Japan Scientific Societies Press, Japan, 1987, pp.29) with the in situ collagenase perfusion. Isolated hepatoc)tes (viability was 88–93%) suspended in 0.5 ml of Williams medium E supplemented with 5% calf serum were plated at a density of 2.5×10$^5$ cells/ml in 24-well plastic dishes (Corning company) and cultured for 24 h at 37° C. After that, the medium was exchanged to serum-free culture medium containing various concentrations of h)drox)proline derivatives (Hyp Ser and Hyp Ser OH) and 5 mM (final concentration) of $CCl_4$. The hepatocytes were further cultured for 24 h and culture medium was collected. GOT (glutamic oxaloacetic transaminase) and LDH (lactic dehydrogenase) were assayed using the appropriate assay kits (Wako Pure Chemical Industries, JP). As the positive control, Hepatocyte Growth Factor (HGF), which is known to be effective for the proliferation and protection of hepatocytes, was used in this experiment. The results were shown in FIG. 10 (GOT) and FIG. 11 (LDH). The values in these results were expressed as average ± SE of three wells. Statistical analysis was performed by Student's t-test to identify significant differences between various treatment groups. Against the control, * expresses p<0.05, and ** p<0.01.

Figure 10:
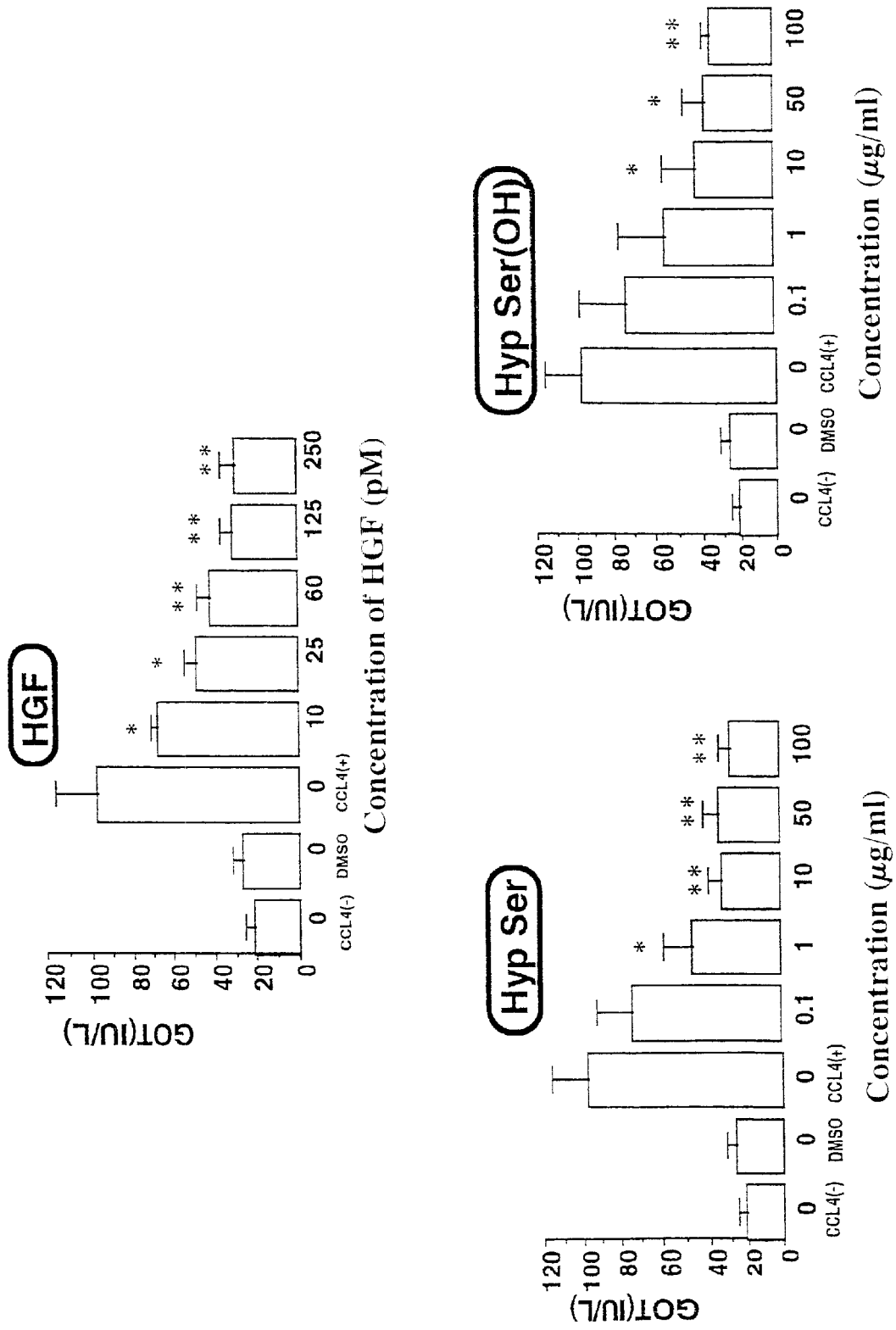
FIG. 10 shows the changes in hepatic cytosolic enzyme (GOT) activity in the medium of $CCl_4$ (carbon tetrachloride)-treated primary cultured rat hepatocytes by the compounds of the invention and HGF (Hepatocyte Growth Factor).

As shown in FIG. 10 and FIG. 11, the hydroxyproline derivatives of the invention decreased the cytosolic enzyme activities of damaged hepatocytes, and thus clearly showed the protective function on hepatocytes.

What is claimed is:

1. A hydroxyproline derivative represented by the general formula (3):

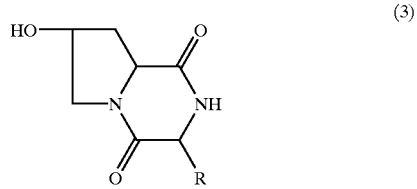

(3)

wherein R is a hydroxymethyl group, wherein the hydroxyproline derivative is essentially pure.

2. A method of treatment of damaged organs and tissues, which comprises:
administering to a mammal in need thereof an effective amount of hydroxyproline derivative represented by the general formula (3):

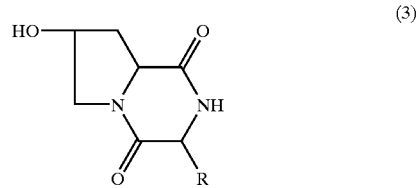

(3)

wherein R is a hydroxymethyl group, wherein the hydroxyproline derivative is administered to a mammal in a concentration of 0.5–100 mg per body weight kg.

3. The method of treatment of damaged organs and tissues according to claim 2, wherein the method is a treatment of a liver disorder.

* * * * *